US008569042B2

(12) United States Patent
Chowdhury et al.

(10) Patent No.: US 8,569,042 B2
(45) Date of Patent: Oct. 29, 2013

(54) DNA STRUCTURES ON FERROELECTRICS AND SEMICONDUCTORS

(75) Inventors: Aref Chowdhury, Springfield, NJ (US); Hock Min Ng, Westfield, NJ (US); Bernard Yurke, Plainfield, NJ (US)

(73) Assignee: Alcatel Lucent, Paris (FR)

( * ) Notice: Subject to any disclaimer, the term of this patent is extended or adjusted under 35 U.S.C. 154(b) by 159 days.

(21) Appl. No.: 11/064,907

(22) Filed: Feb. 23, 2005

(65) Prior Publication Data

US 2006/0210993 A1 Sep. 21, 2006

(51) Int. Cl.

| C12M 1/34 | (2006.01) |
|---|---|
| C12M 1/00 | (2006.01) |
| C12Q 1/68 | (2006.01) |
| G01N 27/00 | (2006.01) |
| G01N 21/00 | (2006.01) |
| H01L 21/20 | (2006.01) |
| C07H 21/02 | (2006.01) |

(52) U.S. Cl.
USPC ... 435/287.2; 435/6.1; 435/283.1; 422/82.01; 422/82.11; 438/483; 536/23.1; 977/924

(58) Field of Classification Search
USPC .................. 435/6.1, 283.1, 287.2; 422/82.01, 422/82.11; 438/483; 536/23.1; 977/924
See application file for complete search history.

(56) References Cited

U.S. PATENT DOCUMENTS

| 5,653,939 | A | * | 8/1997 | Hollis et al. ...................... 506/3 |
|---|---|---|---|---|
| 6,110,749 | A | * | 8/2000 | Obremski et al. ............. 436/527 |
| 6,265,021 | B1 | * | 7/2001 | Black et al. .................... 427/131 |
| 6,274,323 | B1 | * | 8/2001 | Bruchez et al. .............. 435/6.11 |
| 6,569,382 | B1 | * | 5/2003 | Edman et al. ................ 422/68.1 |
| 6,914,279 | B2 | * | 7/2005 | Lu et al. .......................... 506/39 |
| 2001/0006785 | A1 | * | 7/2001 | Ramsey et al. .................... 435/6 |
| 2003/0082633 | A1 | * | 5/2003 | Martin et al. .................. 435/7.1 |
| 2003/0143612 | A1 | * | 7/2003 | Ault-Riche et al. .............. 435/6 |
| 2003/0152930 | A1 | * | 8/2003 | Howard ............................ 435/6 |

FOREIGN PATENT DOCUMENTS

| WO | WO 01/84197 | * | 11/2001 |
|---|---|---|---|
| WO | WO 02/15240 A1 | * | 2/2002 |

OTHER PUBLICATIONS

Hao Yan et al, DNA templated self assembly of protein arrays and highly conductive nanowires, 2003, Science, 301, 1882-1884.*
Ismail et al, Silicon nitride direct binding, 199, Electronic Letters, 26, 1045-1046.*
Periodic Table—Cotton et al.*
Lenigk et al, Surface characterization of a silicon chip based DNA microarray, 2001, Langmuir, 17, 2497-2501.*
Periodic Table Los Alamos Laboratory brochure, Jun. 9, 2010, p. 1.*
Decorate definition brochure, Dictionary.com, printed Jun. 11, 2010, pp. 1-2.*
Silicon wafer semiconductor brochure, printed Jun. 11, 2010, p. 1.*
Datasheet bound, Retrieved from the internet URL:http//dictionary.reference.com/browse/bound; printed Nov. 18, 2010.*
Winfree, et al., "Design and self-assembly of two-dimensional DNA crystals," Nature, vol. 394, pp. 539-544, (Aug. 6, 1998).
Yan, H., et al., "DNA-Templated Self-Assembly of Protein Arrays and Highly Conductive Nanowires," Science, vol. 301, pp. 1882-1884, (Sep. 26, 2003).
Cook, M., et al., "Self-Assembled Circuit Patterns," Lecture Notes in Computer Science, vol. 2943, pp. 91-107, (2004).
Rothemund, P.W.K., et al., "Algorithmic Self-Assembly of DNA Sierpinski Triangles," PLOS Biology, www.plosbiology.org, vol. 2, Issue 12, e424, pp. 2041-2053, (Dec. 2004).
Weizmann, Y., et al., "Amplified detection of DNA and analysis of single-base mismatches by the catalyzed deposition of gold on Au-nanoparticles," Analyst, vol. 126, pp. 1502-1504, (2001).
Elghanian, R., et al., "Selective Colorimetric Detection of Polynucleotides Based on the Distance-Dependent Optical Properties of Gold Nanoparticles," Science, www.sciencemag.org, vol. 277, pp. 1078-1081, (Aug. 22, 1997).
Taton, T.A., et al., "Scanometric DNA Array Detection with Nanoparticle Probes," Science, www.sciencemag.org, vol. 289, pp. 1757-1760, (Sep. 8, 2000).
Yan, H., et al., "DNA-Templated Self-Assembly of Protein Arrays and Highly Conductive Nanowires, Supporting Online Material," published online at www.Sciencemag.org, Science, vol. 301 (Sep. 2003) 12 pages.

* cited by examiner

*Primary Examiner* — Narayan Bhat
(74) *Attorney, Agent, or Firm* — Hitt Gaines, PC

(57) ABSTRACT

An apparatus includes a substrate and a plurality of DNA oligomers in contact with a top surface of the substrate. The substrate is a polar ferroelectric or a polar compound semiconductor.

20 Claims, 4 Drawing Sheets

FIG. 1

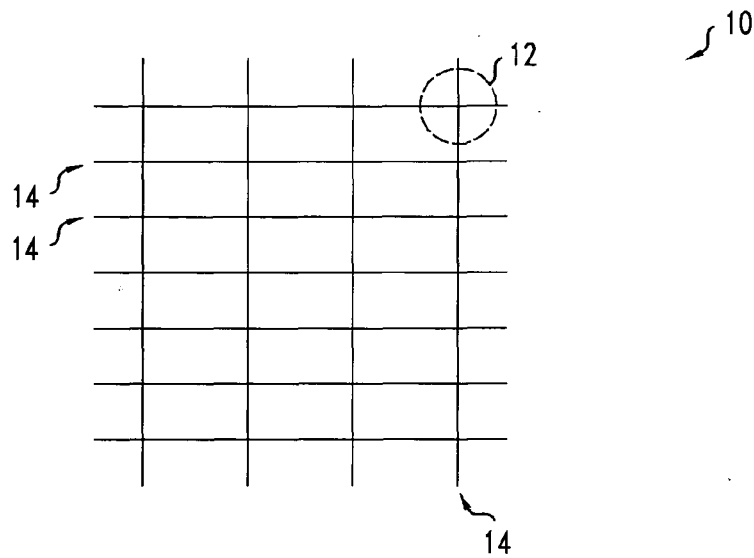

FIG. 2

```
         v                                              r
**ccag ccgcaca ggtagcatcc gcaaggctagt ccgcga tagg    — 1

**cgttgg tgtgcgg    — 2
                                                s
**cctactcatca ggagacctca gaacggtccgt ccaacg cgag    — 3
       w                    r*
**gagg gtgactcggg tgatgagtagg ccta    — 4

**ccatcttgcca ggtcacttca gctaggatcgt cccgagtcag    — 5
      v*                    s*
**ctgg caaccgaagg tggcaagatgg ctcg    — 6
   w*
**cctc acaagca ggttgcctca agacggcatgt ccttcggttg    — 7

**tcgcgg tgcttgt    — 8

**ccgttc tttt tgaggtctcc acgagcctagc tttt tgaagtgacc
   acatgccgtct tttt tgaggcaacc actagccttgc tttt       ⎫
   ggatgctacc acgga                                   ⎬ 9
                                                      ⎭
```

DNA STRUCTURES ON FERROELECTRICS AND SEMICONDUCTORS

BACKGROUND

1. Field of the Invention

The invention relates to optical and electronic devices and to methods for fabricating such devices.

2. Discussion of the Related Art

Recent developments have provided a number of techniques for custom fabricating structures with feature-sizes and feature-separations on the order of a nanometer (nm). The techniques use deoxyribonucleic acid (DNA) tiles to produce structures with such small feature-dimensions. Several articles describe methods for fabricating DNA tiles and larger structures made of DNA tiles. These articles include: "Design and self-assembly of two-dimensional DNA crystals" by Erik Winfree et al, Nature, vol. 394 (1998) pages 539-544; "DNA-Templated Self-Assembly of Protein Arrays and Highly Conductive Nanowires" by Hao Yan et al, Science, vol. 301 (2003) pages 1882-1884 (Herein, referred to as Yan1.); and "DNA-Templated Self-Assembly of Protein Arrays and Highly Conductive Nanowires, Supporting Online Material" by Hao Yan et al, published online at www.Sciencemag.org, Science, vol. 301 (September 2003) 12 pages (Herein, referred to as Yan2.). The three above-listed publications are incorporated herein by reference in their entirety.

FIG. 1 shows a planar DNA structure 10 that can be made from exemplary DNA tiles 12. The exemplary DNA tiles 12 are shaped like crosses. The crosses have several arms 14, and each arm 14 includes more than two strands of DNA.

FIG. 2 shows nucleotide base sequences for nine single-stranded artificial DNA oligomers, i.e., SEQ ID NOs: 1, 2, 3, 4, 5, 6, 7, 8, and 9, that hybridize together to form the exemplary DNA tiles 12 of FIG. 1. In the base sequences, ** indicates the "5" end of the DNA backbone, and a, t, c, and g indicate the respective bases adenine, thymine, cytosine, and guanine. DNA tiles can be made from DNA oligomers with other nucleotide base sequences, e.g., nine DNA oligomers obtained by reversing each nucleotide base sequence of FIG. 2.

During formation of the exemplary DNA tile 12, sixteen nucleotide base subsequences of the DNA oligomers shown in SEQ. ID. Nos. SEQ ID NOs: 1-9 hybridize to complementary nucleotide base subsequences. After formation, the exemplary DNA tiles 12 have unhybridized "t t t t" sequences. The exemplary DNA tiles 12 also have other short unhybridized base sequences r, r*, s, s*, v, v*, w, w* located at lateral edges of the DNA tile 12, i.e., at ends of the cross. Herein, the asterisk "*" indicates a complementary base sequence. The short sequences at the lateral edges of each DNA tile 12 have about 3-5.

Herein, such short unhybridized nucleotide base sequences at the edges of DNA tiles will be referred to as sticky ends. While sticky ends do not hybridize in single DNA tiles, they can hybridize between different DNA tiles to produce larger structures from the DNA tiles, e.g., planar DNA structure 10.

One method for forming planar DNA structure 10 involves performing the following steps. First, an aqueous solution of DNA oligomers is prepared at a temperature of about 80° C.-90° C., e.g., a solution of DNA oligomers defined by SEQ ID NOs: 1-9. In the solution, the DNA oligomers for making a tile have equal molar concentrations. The solution includes, e.g., the buffer Tris to maintain the pH at about 7.6 and also includes suitable amounts of EDTA and magnesium acetate for DNA hybridization. Second, the solution is slowly cooled to room temperature at a cooling rate of about 1 degree centigrade per 1-15 minutes. During early portions of the cooling process, complementary nucleotide base sequences of the DNA oligomers, e.g., DNA oligomers with SEQ ID NOs: 1-9, hybridize with complementary base sequences to form the DNA tiles. During the early part of the cooling, thermal excitations upset weak bonds that may form when the short base sequences of the sticky ends hybridize between different DNA tiles. For that reason, the formation of DNA tiles typically occurs prior to substantial joining of the different DNA tiles. At later parts of the cooling process, the lower temperatures enable the short sticky ends to stably hybridize thereby joining together different DNA tiles, e.g., to form the tiled planar DNA structure 10.

Modifying the individual DNA tiles enables one to predetermine the global form of the structure that will form when the DNA tiles hybridize together. By using a mixture of DNA tiles with different sticky ends, one can predetermine both the size and the shape of final tiled structure. When such mixtures of DNA tiles are used, the above-described method is modified so that the different types of DNA tiles are fabricated separately. Separate fabrication avoids undesired hybridizations between the DNA oligomers for the different types of tiles, i.e., DNA oligomers that different by subsequences for sticky ends. After forming the DNA tiles, the solutions of the different types of DNA tiles are combined and further cooled to produce the desired tiled DNA structure, e.g., planar DNA structure 10.

Referring to FIG. 3, configuration 11 illustrates how control over the global form of a tiled DNA structure can result when different types of DNA tiles 12' are hybridized together. Here, DNA tiles 12' have six different combinations of sticky ends. The combinations of sticky ends were selected to ensure that hybridization of the DNA tiles 12 would produce a rectangle having a length to width ratio of 3:2. In particular, while the DNA tiles 12' have complementary pairs of sticky ends ($\delta$, $\delta^*$), ($\in$, $\in^*$), ($\mu$, $\mu^*$), ($\nu$, $\nu^*$), ($\gamma$, $\gamma^*$), ($\alpha$, $\alpha^*$), ($\beta$, $\beta$), ($\gamma$, $\gamma^*$), other pairings of DNA sticky sequences $\delta$, $\delta^*$, $\in$, $\in^*$, $\mu$, $\mu^*$, $\nu$, $\nu^*$, $\gamma$, $\gamma^*$, $\alpha$, $\alpha^*$, $\beta$, $\beta^*$, $\gamma$, $\gamma^*$, and $\kappa$ do not stably hybridize. For that reason, the different DNA tiles 12' of FIG. 3 will form a single stable configuration, i.e., a 2×3 rectangle, in response to being combined and enabled to hybridize.

Other methods are known for making planar DNA structures with preselected shapes from fewer types of DNA tiles, i.e., fewer combinations of sticky edges. These other methods, e.g., enable the formation of rectangular DNA sheets having various lengths and widths. These methods are, e.g., described in "Self-Assembled Circuit Patterns" by Matthew Cook et al, DNA Computers 9, LNCS, vol. 2943 (2004) pages 91-107; and "Algorithmic Self-Assembly of DNA Serpinsky Triangles" by Paul W. K. Rothemund et al, PloS Biology, vol. 2, issue 12 (2004) pages 2041-2053. Both of the above-listed articles are incorporated herein by reference in their entirety.

A variety of methods are also available for functionalizing individual DNA tiles to bind metal particles.

A first such method involves hybridizing DNA oligomers of FIG. 2, i.e., SEQ. ID. Nos. 1-8, with a new DNA oligomer to form biotin-functionalized DNA tiles and then, binding a gold-labeled protein to these biotin-functionalized DNA tiles. In this method, the new DNA oligomer has the same base sequence as the remaining DNA oligomer of FIG. 2, i.e., SEQ. ID. No. 9, except that one of the unhybridized "t t t t" subsequences is replaced by a "t t biotin t t" subsequence. That is, the new DNA oligomer includes the protein biotin bond to a thymine base. The biotin will bind other proteins such as streptavidin and avidin. When the biotin-functionalized DNA tiles are mixed in solution with gold-labeled streptavidin or gold-labeled avidin, the biotin causes the particles of gold particle to be bound to the DNA tiles. Gold-labeled streptavidin is sold by Molecular Probes, Inc., 29851 Willow Creek Road, Eugene, Oreg. 97402 USA (www.probes.com). Relevant products are catalog numbers A32360 and A32361 for the ALEXA FLUOR® 488 streptavidin colloidal gold conjugates and catalog numbers A24926 and A24927 for the ALEXA FLUOR® 488 and 595 FLUORNANOGOLD™ conjugates with gold particles. Gold-labeled avidin is available from Sigma-Genosys, 1442 Lake Front Circle, The Woodlands, Tex. 77380 USA (www.sigma-genosys.com).

A second such method involves functionalizing one or more of the constituent DNA oligomers with a thiol group and then, using the thiol group to chemically bind a gold particle. Methods for adding a thiol group to one end of a DNA oligomer are known to those of skill in the art. One or more of the DNA oligomers SEQ ID NOs: 1-8 of FIG. 2 may be functionalized with thiol groups prior to formation of the DNA tiles. Alternately, one of the DNA oligomers of SEQ ID NOs: 1-8 may be replaced by two shorter DNA oligomers where one of the shorter DNA oligomers is functionalized by a thiol group. After making DNA tiles with DNA oligomers functionalized by the thiol groups, gold particles are added to the solution of functionalized DNA tiles. The thiol groups will cause the gold particles to be chemically bonded to the DNA tiles.

In a third method, the DNA tiles are fabricated with an extra base sequence that does not hybridize during tile-formation. Then, complementary base sequences having attached gold particles are mixed with a solution of the formed DNA tiles. The complementary base sequences bind to the DNA tiles thereby binding the gold particles to said DNA tiles.

BRIEF SUMMARY

Various embodiments provide for hybrid devices in which a DNA structure decorated by an electrical or optical element is combined with a non-DNA based structure. In said hybrid devices, feature sizes may be very small, because features of the DNA structure are made via DNA technology rather than by conventional lithography.

In one aspect, the invention features an apparatus that includes a substrate and a plurality of DNA oligomers in contact with a top surface of the substrate. The substrate is a polar ferroelectric or a polar compound semiconductor.

In another aspect, the invention features a method. The method includes depositing a quantity of aqueous solution on a surface of a polar ferroelectric or a polar compound semiconductor. The solution includes DNA.

In another aspect, the invention features an apparatus that includes a substrate and a plurality of DNA structures. The substrate is a polar ferroelectric or a polar compound semiconductor. The substrate has a top surface and is hydrophilic. The DNA structures are in contact with the top surface. The DNA structures are patterned with metal, quantum dots, or dye molecules.

BRIEF DESCRIPTION OF THE DRAWINGS

FIG. 1 is a top view of a planar DNA structure formed of cross-shaped DNA tiles;

FIG. 2 shows nucleotide base sequences for DNA oligomers, i.e., SEQ ID NOs: 1, 2, 3, 4, 5, 6, 7, 8, and 9, for exemplary DNA tiles for forming the planar DNA structure of FIG. 1;

The illustrative embodiments are described more fully by the Figures and detailed description. The inventions may, however, be embodied in various forms and are not limited to the embodiments described in the Figures and detailed description.

DETAILED DESCRIPTION OF ILLUSTRATIVE EMBODIMENTS

Figure 3:
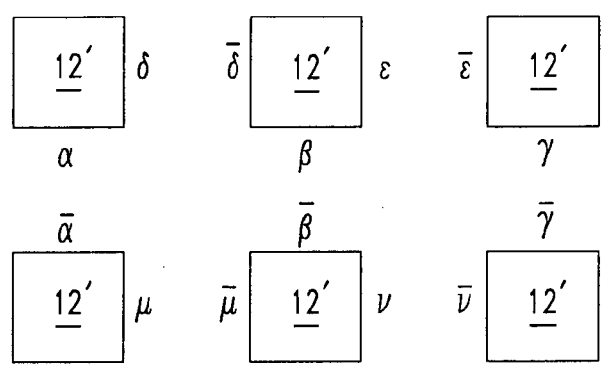
FIG. 3 illustrates a configuration of DNA tiles in a DNA rectangle wherein the combinations of sticky ends of the DNA tiles causes the DNA tiles to self-assemble into the rectangle.
Figure 4:
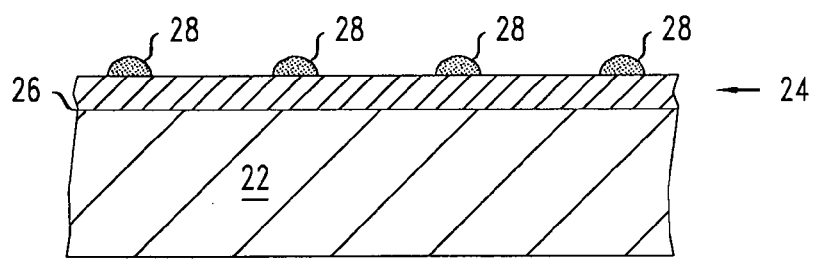
FIG. 4 is a cross-sectional view of a portion of a hybrid structure that incorporates DNA, e.g., a tile-based planar DNA structure.

FIG. 4 shows a portion 20 of a hybrid optical or electronic device. The hybrid device includes a ferroelectric or semiconductor substrate 22 and a layer 24 of DNA deposited on a top surface 26 of the substrate 22. The substrate 22 is a polar material and is preferably hydrophilic. The substrate 22 creates an electrostatic force that holds portions of the DNA molecules in contact with the top surface 26 without covalent bonding. While portions of the DNA molecules of the layer 24 are electrostatically held to the top surface 26, other portions of the DNA molecules may be able to move with respect to the top surface 26.

The layer 24 of DNA molecules has a pattern of optical or electrical features 28 thereon. The features 28 may include metal particles, metal wires, man-made quantum dots, and/or dye molecules. In exemplary embodiments where the features 28 are metal wires or metal particles, the particles or wires may include silver, gold, platinum, copper, palladium, or a combination of these metals.

In some embodiments, the layer 24 of DNA molecules is a monolayer of tile-based planar DNA structures, e.g., planar DNA rectangles 10 as shown in FIG. 1 and described in the background section and artificial planar DNA structures of other shapes. The planar DNA structures are patterned by the functional features 28, i.e., metal particles, metal wires, quantum dots, and/or dye molecules. The features 28 are typically bound to the individual DNA tiles that form the planar DNA structures. For that reason, the features 28 can be distributed in a regular array whose period is fixed by the dimensions of individual DNA tiles. For that reason, the spacing of the features 28 may be of the order of one or a few nanometer. In light of the above-described methods for tile-based fabrication of planar DNA structures, one of skill in the art would be able to fabricate such planar DNA structures.

With respect to fabricating such planar DNA structures patterned by metal particles or wires, this can be achieved by combining the tile-based methods for fabricating planar DNA structures, e.g., DNA rectangles, with methods for functionalizing individual DNA tiles. The tile-based methods for fabricating planar DNA structures position specific types of DNA tiles, i.e., tiles with specific combinations of sticky edges, at specific positions on the planar DNA structures. Thus, a selected pattern of optical or electrical features may be obtained by separately fabricating different types of DNA tiles, i.e., DNA tiles having different features and sticky end combinations, and then, combining the different DNA tiles to produce the desired patterned planar DNA structure. During fabrication of the DNA tiles, functional moieties are bonded to the specific DNA tiles that will be positioned at the desired locations for metal particles in the final patterned planar DNA structure. After being separately functionalized, the different types of DNA tiles can be mixed together to form a patterned planar DNA structure via inter-tile hybridization.

With respect to patterning the planar DNA structure with metal wires, a variety of methods are available for growing metal on seed particles of gold that are themselves already bonded to DNA tiles. Such growth could, e.g., produce connections between the metal particles on adjacent DNA tiles thereby forming metallic wires. One example of such a method involves performing electroless deposition of gold onto small gold particles that are already attached to the DNA tiles. This method is described in the article "Amplified detection of DNA and analysis of single-base mismatches by the catalyzed deposition of gold on AU-nanoparticles" by Yossi Weizmann et al, Analyst, Vol. 126 (2001) pages 1502-1504, which is incorporated herein by reference in its entirety. Another example of such a method involves growing silver on gold particles that are themselves attached to DNA tiles. The method uses, e.g., the LI Silver Enhancement Kit (L-24919) sold Molecular Probes Inc. These methods can increase sizes of the metal particles already bonded to the DNA tiles so that the metal particles on adjacent DNA tiles will come into physical contact. Such methods can be used to build a wire array on the tile-based planar DNA structure.

With respect to patterning the planar DNA structure by quantum dots, such patterning may be performed with quantum dots that are attached to streptavidin. Quantum dot-labeled streptavidin will bond to individual DNA tiles functionalized with biotin as already described with respect to attaching gold particles. Quantum dots attached to streptavidin are commercially available from the Quantum Dot Corporation of 26118 Research Road, Hayward, Calif. 94545 USA (www.qdots.com). Among this corporation's Bio-labeling products are Qdot Streptavidin and Biotin Conjugates, e.g., catalog product numbers 1010-1 through 1017-1. After being separately functionalized, the different types of DNA tiles can be mixed together for use in a process that forms the patterned planar DNA structure via inter-tile hybridization.

With respect to patterning the planar DNA structure by dye molecules, such patterning may be performed with dye functionalized DNA. Integrated DNA Technologies of 1710 Commercial Park • Coralville, Iowa 52241 (idtdna.com) offers a variety of fluorophores and also offers commercial services for attaching said fluorophores to DNA oligomers. The resulting dye-functionalized DNA oligomers could be attached to individual DNA tiles by modifications of the above-described methods for attaching metal-functionalized DNA strands to DNA tiles. After being separately functionalized, the different types of DNA tiles can be mixed together for use in a process that forms the patterned planar DNA structure via inter-tile hybridization.

Figure 5:
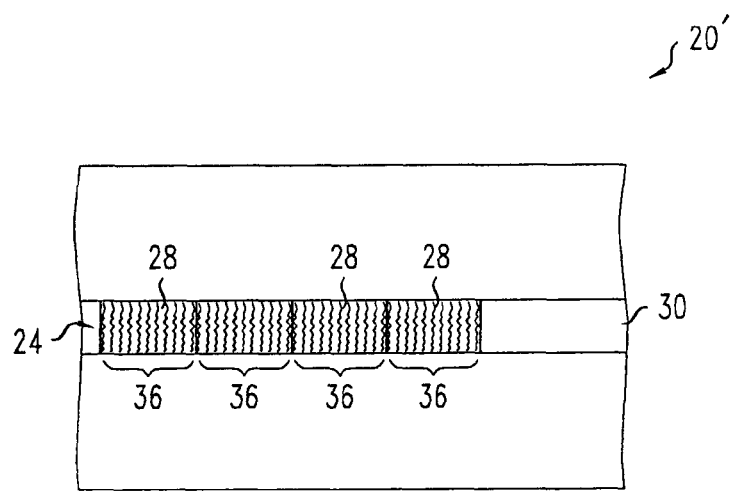
FIG. 5 is a top view of an embodiment of the hybrid structure of FIG. 4 that forms a hybrid optical waveguide device.
Figure 6:
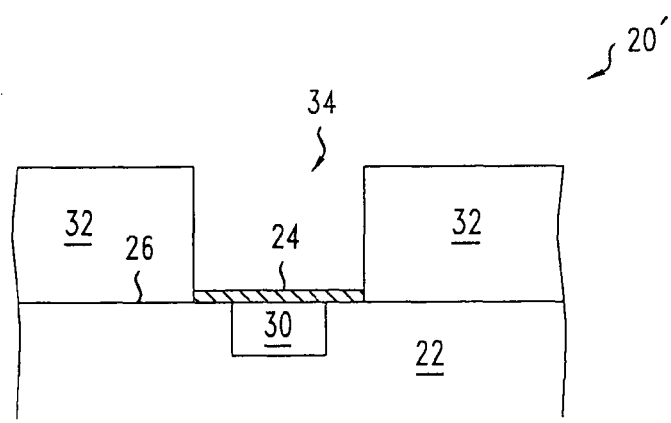
FIG. 6 is a cross-sectional end-view of the hybrid optical waveguide device of FIG. 5.

FIGS. 5 and 6 illustrate an embodiment of a hybrid device 20' that functions as an optical waveguide device. The hybrid device 20' includes an optical waveguide core 30 that is located in the substrate 22. For example, the optical core may be a region of the substrate 22 that has been doped to increase its refractive index relative to the refractive index of surrounding portions of the substrate 22. The substrate 22 and optical waveguide core 30 are formed of a polar material that is preferably also hydrophilic.

Exemplary materials for the substrate 22 and optical waveguide core 30 include ferroelectrics and compound semiconductors. A strongly electrically polarizable ferroelectric such as lithium niobate ($LiNbO_3$) may be used for the substrate 22 and optical core 30. Other candidate strongly polarizable ferroelectrics are barium titanate ($BaTiO_3$), lead titanate ($PbTiO_3$), potassium niobate ($KNbO_3$), lead cobalt tungstate ($Pb(Co_{1/2}/W_{1/2})O_3$), lead iron tantalate ($Pb(Fe_{1/2}/Ta_{1/2})O_3$), lead magnesium niobate ($Pb(Mg_{1/3}Nb_{2/3})O_3$), lead zinc niobate ($Pb(Zn_{1/3}Nb_{2/3})O_3$), lithium tantalate ($LiTaO_3$), potassium strontium niobate, sodium strontium niobate ($NaSr_2Nb_5O_{15}$), lithium potassium strontium niobate ($LiNaSr_4Nb_{10}O_{30}$), sodium barium niobate ($NaBa_2Ni_5O_{15}$), barium strontium niobate, potassium lithium niobate ($K_3Li_2Nb_5O_{15}$), bismuth titanate ($Bi_4Ti_3O_{12}$), and potassium dihydrogen phosphate ($KH_2PO_4$). Candidate compound semiconductors include some crystalline group III-V and group II-VI semiconductors. Candidates include some hydrophilic compound semiconductors with the formulas $Al_xGa_{(1-x)}N$, $ZnO$, $Mg_xZn_{(1-x)}O$, $Cd_xZn_{(1-x)}O$ with $0 \le x \le 1$. For example, aluminum-containing nitride semiconductors can be hydrophilic.

The hybrid optical device 20' includes a sequence of tile-based DNA structures 36, which are located along the axis of the optical core 30. The hybrid optical device 20' also includes a hydrophobic dielectric layer 32, e.g., a layer of a non-polar photoresist. Please replace the paragraph beginning at page 9, line 17 with the following amended paragraph:

The hydrophobic dielectric layer 32 has one or more vias or trenches 34 that pass through the layer 32. The vias or trenches 34 are located along the optical waveguide core 30. The bottom surface of the vias or trenches 34 expose a portion of or all of the top surface 26 of the optical waveguide core 30. The bottom surface of the trench 34 is covered by a monolayer of tiled-based planar DNA rectangles 36. The tile-based DNA rectangles 36 may be patterned with quantum dots, dye molecules, metal particles, or metallic wires as already described. The patterned DNA rectangles 36 are located close enough to the optical waveguide core 30 to affect evanescent optical fields produced during light transmission along the optical waveguide core 30.

During fabrication, the trench 34 functions to align the planar DNA rectangles 36 with respect to the axis of the optical waveguide core 30. In particular, the dielectric layer 32 is a non-polar and/or hydrophobic material. Thus, the dielectric layer 32 is either not wetted by the aqueous solution used to deposit the planar DNA rectangles 36 or does not electrostatically bind the DNA therein during deposition of an aqueous solution of said DNA rectangles 36 on the dielectric-patterned substrate. In contrast, the substrate 22 and waveguide core 30 are hydrophilic and polar so that such an aqueous solution of the planar DNA rectangles 36 will wet their top surface 26 thereby enabling electrostatic forces to bind the planar DNA rectangles 36 to exposed portions of the top surface 26 during such a liquid-based fabrication.

The planar DNA rectangles 36 have a side length that is selected to be near and slightly smaller than to the width of the via or trench 34. The side length is sufficiently close to the width of the via or trench 34 that the via or trench 34 aids in aligning the planar DNA rectangles 36 during the self-assembly of layer 24, which results when a solution of the planar DNA rectangles 36 is deposited over the dielectric-patterned substrate. In particular, during such a fabrication step, the deposited DNA rectangles 36 will relax towards the bottom of the trench 34 and will take up positions that are substantially aligned due to the narrowness of the via or trench 34 and the hydrophobic nature of the dielectric layer 32. Thus, corresponding features on different ones of the planar DNA substrates 36 will become aligned during fabrication due to the via or trench 34.

In some embodiments, the planar DNA structures 36 produces a medium that changes optical properties of the optical waveguide having optical waveguide core 30. For example, the planar DNA structures 36 may be patterned with metallic wire arrays and function as an optical grating for light propagating in the optical waveguide. In particular, the sequence of said planar DNA rectangles 36 can form a single 1-dimensional optical grating due in part to the inter-rectangle alignment provided by the via or trench 34. Nevertheless, the Bragg length of such an optical grating can be as small as individual DNA tiles and sequences thereof rather than by being limited to the larger size of the planar DNA rectangles 36.

In some embodiments, the substrate 22 with optical core 30 are formed of a nonlinear optical material. For example the substrate 22 and core 30 may regions of a z-cut lithium niobate crystal. Such crystals are available from Crystal Technology Inc., CA USA (www.crystaltechnology.com). In such embodiments, the tile-based DNA structures 36 are deposited on a +z surface of the lithium niobate crystal to form hybrid device 20'. In particular, DNA electrostatically binds more strongly to the +z surface of z-cut lithium niobate than to some other surfaces of such crystals.

Figure 7:
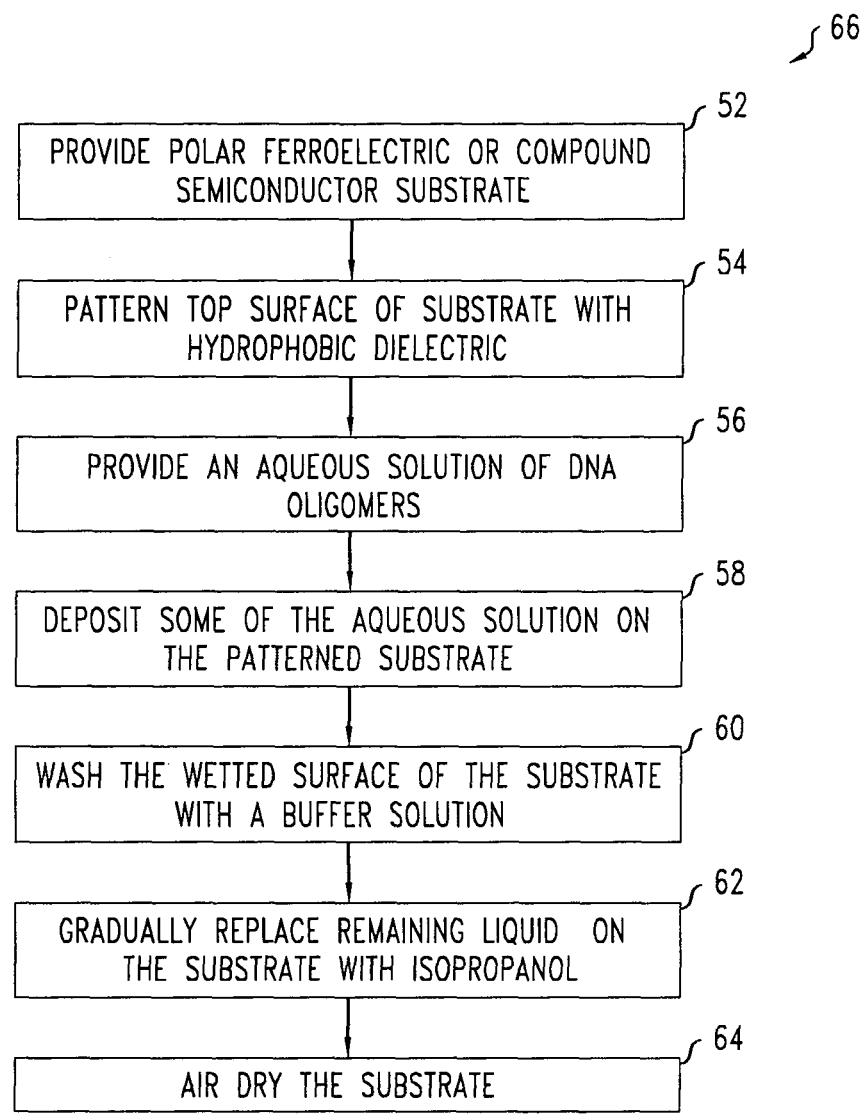
FIG. 7 is a flow chart illustrating one method of fabricating the hybrid optical waveguide device of FIGS. 5 and 6.

FIG. 7 illustrates one method 50 for fabricating a hybrid electrical or optical device, e.g., hybrid optical device 20' of FIGS. 5 and 6.

The method 50 includes providing a polar ferroelectric substrate or a polar compound semiconductor substrate with a top surface (step 52). Typically, the top surface of the substrate is also hydrophilic. The substrate may include a functional electronic or optical device, which is close enough to the top surface be influenced by electrical or optical structures on the top surface. For example, the optical waveguide core 30 of FIG. 6 is close enough to structures on top surface 26 so that such structures can affect light propagation in the optical waveguide core 30.

The method 50 includes patterning the top surface with a hydrophobic dielectric layer, e.g., a non-polar dielectric, to produce protected regions on the top surface (step 54). The patterning produces one or more vias or trenches that expose a portion of the top surface of the substrate, e.g., a portion of the top surface adjacent an underlying electrical or optical structure in the substrate. An exemplary via or trench is the via or trench of FIG. 6, which exposes the optical waveguide core 30. An exemplary patterning step involves depositing a layer of hydrophobic photoresist on the top surface, lithographically patterning the photoresist, and then, developing the photoresist to produce the one or more vias or trenches therein.

The method 50 includes providing an aqueous solution of DNA oligomers (step 56). The DNA oligomers, e.g., belong to the DNA tiles of a planar DNA structure as already described. Some of said DNA oligomers may be functionalized with metal, quantum dots, or dye molecules. For example, some of the tiles of the planar DNA structure may have DNA strands that are functionalized and thus, bind metal, quantum dots, or dye molecules. The aqueous solution is maintained at conditions suitable for hybridization of sticky ends of the DNA tiles so that the planar DNA rectangles are stable in the solution. That is, the aqueous solution should be suitable for DNA hybridization, e.g., a buffered solution with a pH of about 8 and about 0.05-0.1 molar magnesium acetate.

The method 50 includes depositing some of the aqueous solution on the patterned top surface of the patterned substrate (step 58). The deposited solution will wet the exposed portion of the polar substrate thereby enabling the DNA oligomers to come into contact with exposed portions of the substrate. After performing the depositing step, the method 50 may involve waiting five or more minutes if the DNA oligomers belong to tile-based DNA structures. The wait period should enable such DNA-structures to self-assemble under electrostatic forces exerted by exposed portions of the polar substrate thereby forming a monolayer on said substrate.

Next, the method 50 includes washing the wetted surface with a buffer solution, e.g., a solution with a pH of about 8 (step 60). The wash step removes DNA oligomers that are not electrostatically bound to the polar substrate. During the wash step, some bound DNA may move to more stable positions on the polar substrate, e.g., to increase the amount of contact with the polar substrate.

The method 50 includes gradually adding isopropanol to the liquid remaining on the substrate (step 62). The addition step may, e.g., increase the percentage of isopropanol by about 10% per minute until the liquid is essentially isopropanol. Due to isopropanol's lower surface tension, surface effects are less likely to disturb the electrostatically bound layer of DNA during subsequent treatment than would be the case if remaining liquid was primarily water.

Finally, the method 50 includes air drying the substrate to remove the isopropanol (step 64). During the air drying, electrostatic forces keep the DNA bound to polar substrate. Typically, the drying involves passing an air current over the substrate.

From the disclosure, drawings, and claims, other embodiments of the invention will be apparent to those skilled in the art.

What we claim is:

1. An apparatus, comprising:
a substrate that is a polar ferroelectric or a polar compound semiconductor, the substrate having a top surface and being hydrophilic; and
a two-dimensional array of DNA tiles being in contact with exposed portions of said top surface, each DNA tile of the array having sticky ends of single stranded DNA hybridized to sticky ends of single stranded DNA of others of the DNA tiles of the array some of the DNA tiles being patterned with metal, quantum dots, or dye molecules; and wherein the substrate comprises an optical waveguide, the DNA tiles being adjacent to a side surface of the optical waveguide.

2. The apparatus of claim 1, further comprising a hydrophobic layer located on said top surface, the DNA tiles being located in a trench through said hydrophobic layer.

3. The apparatus of claim 1, wherein the substrate is a ferroelectric.

4. The apparatus of claim 1, wherein the substrate is a polar ferroelectric.

5. The apparatus of claim 1, wherein the substrate is a polar compound semiconductor.

6. An apparatus, comprising:
a substrate that is a polar ferroelectric or a polar compound semiconductor, the substrate having a top surface; and
a two-dimensional array of DNA tiles being in contact with exposed portions of said top surface, each DNA tile of the array having sticky ends of single stranded DNA hybridized to sticky ends of single stranded DNA of others of the DNA tiles of the array; and
wherein the substrate comprises an optical waveguide, the array being adjacent a surface of the optical waveguide.

7. The apparatus of claim 6, wherein the substrate is a polar ferroelectric.

8. The apparatus of claim 6, wherein the substrate is a polar compound semiconductor.

9. An apparatus, comprising:
a substrate that is a polar ferroelectric or a polar compound semiconductor, the substrate having a top surface; and
a regular two-dimensional array of DNA tiles being in contact with exposed portions of said top surface, each DNA tile of the array having sticky ends of single stranded DNA hybridized to sticky ends of single stranded DNA of others of the DNA tiles of the array; and
a hydrophobic layer located on said top surface, the hydrophobic layer having at least one trench formed therethrough thereby exposing the top surface, the array being located in the trench on the top surface.

10. The apparatus of claim 9, wherein the substrate is a polar ferroelectric.

11. The apparatus of claim 9, wherein the substrate is a polar compound semiconductor.

12. An apparatus, comprising:
a substrate that is a polar ferroelectric or a polar compound semiconductor, the substrate having a top surface; and
a regular two-dimensional array of DNA tiles being in contact with exposed portions of said top surface, each DNA tile of the array having sticky ends of single stranded DNA hybridized to sticky ends of single stranded DNA of others of the DNA tiles of the array; and
wherein one of the DNA tiles includes an optical or electrical feature chemically bonded thereto, each feature being selected from the group consisting of a metal particle, metal wire, and a quantum dot.

13. The apparatus of claim 12, wherein the substrate is a polar ferroelectric.

14. The apparatus of claim 12, wherein the substrate comprises one of barium titanate and lithium niobate.

15. The apparatus of claim 12, wherein the substrate comprises a group III-V compound semiconductor.

16. The apparatus of claim 15, wherein the group III-V compound semiconductor comprises aluminum.

17. The apparatus of claim 12, wherein the substrate is a polar compound semiconductor.

18. The apparatus of claim 12, wherein the chemical bonding includes a functionalizing moiety.

19. The apparatus of claim 18, wherein the functionalizing moiety includes one of streptavidin or biotin.

20. An apparatus, comprising:
a substrate that is a polar ferroelectric or a polar compound semiconductor, the substrate having a top surface; and a two-dimensional array of DNA tiles being in contact with exposed portions of said top surface, each DNA tile of the array having sticky ends of single stranded DNA hybridized to sticky ends of single stranded DNA of others of the DNA tiles of the array; and wherein one of the DNA tiles includes an optical or electrical feature chemically bonded thereto, each feature being selected from the group consisting of a metal particle, metal wire, a quantum dot, and a dye molecule, and a second of the DNA tiles includes an optical or electrical feature chemically bonded thereto, the feature bonded to the second of the DNA tiles being selected from the group consisting of a metal particle, metal wire, a quantum dot, and a dye molecule, a spacing of the features is of the order of 1 nanometer.

* * * * *

SEQUENCE LISTING

<160> NUMBER OF SEQ ID NOS: 9

<210> SEQ ID NO 1
<211> LENGTH: 42
<212> TYPE: DNA
<213> ORGANISM: Artificial Sequence
<220> FEATURE:
<223> OTHER INFORMATION: Description of Artificial Sequence: synthetic
      DNA sequence

<400> SEQUENCE: 1
ccagccgcac aggtagcatc cgcaaggcta gtccgcgata gg                        42

```
<210> SEQ ID NO 2
<211> LENGTH: 13
<212> TYPE: DNA
<213> ORGANISM: Artificial Sequence
<220> FEATURE:
<223> OTHER INFORMATION: Description of Artificial Sequence: synthetic
      DNA sequence

<400> SEQUENCE: 2
cgttggtgtg cgg                                                              13

<210> SEQ ID NO 3
<211> LENGTH: 42
<212> TYPE: DNA
<213> ORGANISM: Artificial Sequence
<220> FEATURE:
<223> OTHER INFORMATION: Description of Artificial Sequence: synthetic
      DNA sequence

<400> SEQUENCE: 3
cctactcatc aggagacctc agaacggtcc gtccaacgcg ag                              42

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: synthetic
      DNA sequence

<400> SEQUENCE: 4
gagggtgact cgggtgatga gtaggccta                                            29

<210> SEQ ID NO 5
<211> LENGTH: 42
<212> TYPE: DNA
<213> ORGANISM: Artificial Sequence
<220> FEATURE:
<223> OTHER INFORMATION: Description of Artificial Sequence: synthetic
      DNA sequence

<400> SEQUENCE: 5
ccatcttgcc aggtcacttc agctaggatc gtcccgagtc ag                              42

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: synthetic
      DNA sequence

<400> SEQUENCE: 6
ctggcaaccg aaggtggcaa gatggctcg                                            29

<210> SEQ ID NO 7
<211> LENGTH: 42
<212> TYPE: DNA
<213> ORGANISM: Artificial Sequence
<220> FEATURE:
<223> OTHER INFORMATION: Description of Artificial Sequence: synthetic
      DNA sequence

<400> SEQUENCE: 7
cctcacaagc aggttgcctc aagacggcat gtccttcggt tg                              42

<210> SEQ ID NO 8
```

-continued

```
<211> LENGTH: 13
<212> TYPE: DNA
<213> ORGANISM: Artificial Sequence
<220> FEATURE:
<223> OTHER INFORMATION: Description of Artificial Sequence: synthetic
      DNA sequence

<400> SEQUENCE: 8
tcgcggtgct tgt                                                            13

<210> SEQ ID NO 9
<211> LENGTH: 100
<212> TYPE: DNA
<213> ORGANISM: Artificial Sequence
<220> FEATURE:
<223> OTHER INFORMATION: Description of Artificial Sequence: synthetic
      DNA sequence

<400> SEQUENCE: 9 ccgttcttttt tgaggtctcc acgagcctag cttttttgaag tgaccacatg                  50 ccgtcttttt tgaggcaacc actagccttg cttttggatg ctaccacgga                    100
```